United States Patent
Bhushan et al.

[11] Patent Number: 5,869,697
[45] Date of Patent: Feb. 9, 1999

[54] PROCESS FOR PREPARING DILTIAZEM

[75] Inventors: Lohray Braj Bhushan; Balakrishnan Ezhuthachan Jayachandran; Lohray Vidya Bhushan; Ravindranathan Thottappillil, all of Pune, India

[73] Assignee: Council of Scientific & Industrial Research, India

[21] Appl. No.: 882,387

[22] Filed: Jul. 7, 1997

Related U.S. Application Data

[63] Continuation of Ser. No. 605,699, Feb. 23, 1996, abandoned, which is a continuation of Ser. No. 236,204, May 2, 1994, abandoned.

[51] Int. Cl.$^6$ ...................... C07D 317/34; C07D 327/10
[52] U.S. Cl. .............................................. 549/34; 549/229
[58] Field of Search ........................................ 549/229, 34

[56] References Cited

U.S. PATENT DOCUMENTS

| | | | |
|---|---|---|---|
| 4,663,467 | 5/1987 | Kruper, Jr. et al. | 549/229 |
| 5,023,342 | 6/1991 | Sharpless et al. | 549/34 |
| 5,272,270 | 12/1993 | Hirsenkorn et al. | 546/141 |

FOREIGN PATENT DOCUMENTS

| | | | |
|---|---|---|---|
| 0471303 | 2/1992 | European Pat. Off. | C07D 217/24 |

OTHER PUBLICATIONS

Carey, F. A. et al. *Advanced Organic Chemistry Part A:Structure and Mechanisms* (Plenum Press, N.Y.), pp. 258–261 (1990).

Solomons, T.W.G. *Organic Chemistry* (John Wiley & Sons, N.Y.), p. 242 (1992).

*Primary Examiner*—John M. Ford
*Attorney, Agent, or Firm*—Schweitzer Cornman Gross & Bondell LLP

[57] ABSTRACT

A compound of formula (IV)

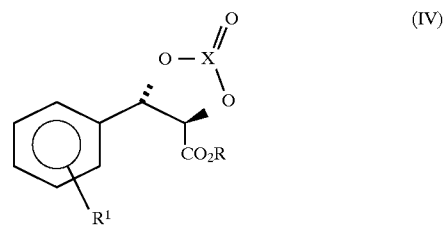

wherein $R^1$ is hydrogen, an alkyl, alkoxy, alkylamino, alkylthio, aryl, aryloxy, or halogen residue; R is an alkyl, or aryl residue, and X is S or C, which is a valuable intermediate for producing Diltiazem.

7 Claims, No Drawings

PROCESS FOR PREPARING DILTIAZEM

This is a continuation of patent application Ser. No. 08/605,699, filed on Feb. 23, 1996; now abandoned, which is a continuation of grandparent patent application Ser. No. 08/236,204 filed May 2, 1994 now abandoned.

FIELD OF THE INVENTION

The present invention relates to a process for preparing diltiazem, and novel intermediates for use in that process, and to their preparation.

BACKGROUND OF THE INVENTION

Diltiazem, is a compound of the type of formula (VI)

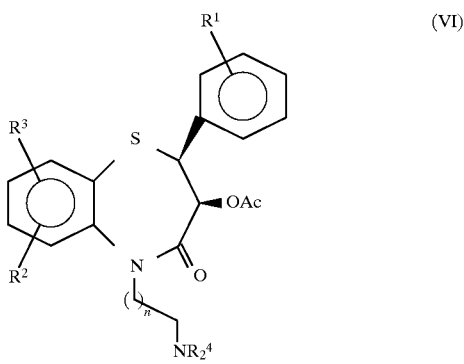

More specifically, Diltiazem is (2S-cis)-3-(acyloxy)-5-[2-(dimethylamino)ethyl]-2,3-dihydro-2-(4-methoxyphenyl)-1.,5-benzothiazepin-4(5H)-one of the formula

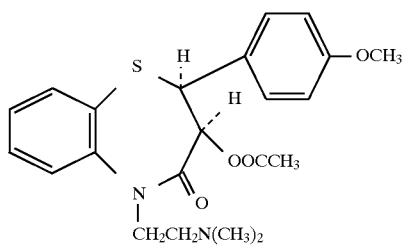

Diltiazem is the highest selling chiral cardiac prescription drug which is synthesized by resolution methods. A number of methods for its resolution are known in the literature.

A few chiral syntheses of diltiazem are known and some of these are described below. One process for the preparation of Diltiazem involves resolution of the key intermediate (αS,βS)-β[(2-aminophenyl)thio]-α-hydroxy-β-(4-methoxyphenyl) propanoic acid alkyl ester of formula (V).

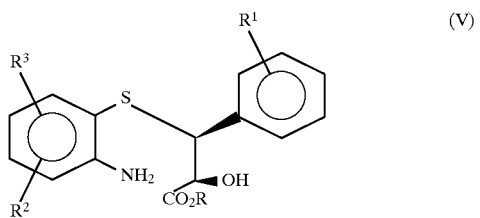

The process is described by Senuma, M.; Shibazaki, M.; Nishimoto, S.; Shibata, K.; Okamura, K.; Date, T.; in Chem. Pharm. Bull. 1989, Vol. 37, P. 3204; U.S. Pat. No. 4,416,819 of Tanabe Seiyaka Co., Ltd.; and in Chem. Abstr. 100, P 85733a; or by a stereoselective synthesis of cis-phenylglycidic acid esters as described by Jgarash, K.:

Honma, T.: in German Patent No. 3,415,035 of Shionogi & Co. Ltd. and Chem. Abstr. 102, p185114f, followed by a stereo- and regioselective opening of the epoxide with either 2-aminothiophenol as described by Hulshof, L. A. ; Roskam, J. . Chem; Schwartz A., in U.S. patent application Ser. No. 197,934 of 1988; Eur. Pat. No. 343,714 of 1989; Chem. Abstr., 1989, 113,77912, or 2-nitrothiophenol as described by Miyazak, M.; Iwakuma, T.; Tanaka, T., Tanabe Seiyaku Co. Ltd., in Chem. Pharm. Bull., 1978, Vol. 26, P. 2889.

More recently, optically active trans-phenylglycidic acid esters were prepared using a stoichiometric amount of a chiral auxiliary followed by a stereoselective opening of the epoxide by various substituted aminothiophenol to give the desired intermediate ester of formula (V) as described by Schwartz. A.; Madan, P. B.; Monacsi, E: O'Brien, J. P.; Todaro, L. J.; Coffen, D. L., in J. Org. Chem 1992, Vol. 57, P. 851.

Alternatively, a stereoselective Michael addition to an (α,β-unsaturated carbonyl compound leading to the derivative of formula (V) has been reported by Miyata, O.; Shinada, T.; Ninomiya, 1.; Nsito, T., in Tetrahedron Lett. 1991, Vol. 32, P. 3519. The compound of formula (V) was converted into Diltiazem of formula (VI) in four steps:

(i) Hydrolysis of the ester to free carboxylic acid.

(ii) Cyclizing the free carboxylic acid to (2S-cis)-(3-hydroxy)2,3-dihydro-2-(4-methoxyphenyl)-1,5-benzothiazepine-4(5H)-one.

(iii) Acetylating the benzothiazepinone with acetic anhydride and pyridine to (2S-cis)-3-(acetyloxy)-2,3-dihydro-2-(4-methoxyphenyl)-1,5-benzothiazepine-4 (5H)-one.

(iv) Converting the benzothiazepinone from step (iii) to Diltiazem of formula (VI) by treating it with a N, N-dialkyl alkyl halide in presence of a suitable base and a suitable solvent All the above procedures have one or more drawbacks:

(i) They involve resolution of either the key intermediate of formula (V) or of the final product Diltiazem of formula (VI).

(ii) In most of the known stereochemical syntheses, a chiral auxiliary is used in stoichiometric amount.

(iii) cis-p-methoxycinnamyl esters are prepared in several steps and it is uneconomical to get them in their stereomerically pure form.

(iv) Asymmetric epoxidation of cis-p-methoxycinnamyl esters involves expensive chiral auxiliaries and even catalytic method of synthesizing these epoxides requires at least 20% of the catalyst.

(v) When trans-p-methoxycinnamyl esters are used, they are converted into epoxides with a stoichiometric amount of a chiral auxiliary, and upon nucleophilic opening with 2-aminothiophenol or 2-nitrothiophenol the epoxides produce both desired and undesired intermediates of formula (V).

(vi) In the synthesis using trans-p-methoxycinnamyl esters, the esters, are first dihydroxylated to furnish a diol of formula (III)

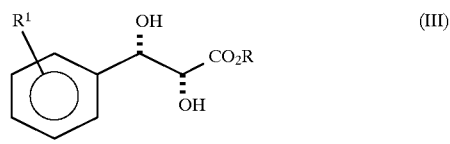

wherein $R^1$ is a methoxy, and R an ethyl residue. The diol of formula (III) is then transformed to a cis-epoxide in two steps. The cis-epoxide then undergoes nucleophilic ring opening to produces the desired intermediate of formula (V).

DESCRIPTION OF THE INVENTION

An object of the present invention is to provide a novel 5S-(p-alkoxyphenyl)-4R-carbalkoxy-1,2,3-dioxathiolene-2-oxide of formula (IV)

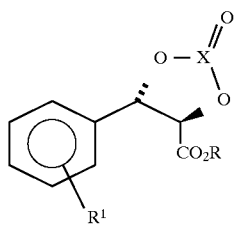

(IV)

wherein $R^1$ is hydrogen, or a hydroxy, alkoxy, alkyl, alkylthio, alkylamino, aryl, or aryloxy residue, suitably a methyl, ethyl, propyl, napthyl, phenyl, 1,2-naphthyl, methoxy, ethoxy, halogen, or a phenoxy residue.

R is an alkyl or an aryl residue, suitably a methyl ethyl, or benzoyl residue; and X is S or C.

For the synthesized Diltiazem $R^1$ is most suitably a methoxy residue and R is most suitably ethyl.

Another object of the present invention is to provide a process for the preparation of the compound of formula (IV) by a stereoselective and easy method. The compound of formula (IV) is a key intermediate in the stereoselective synthesis of the amino ester of formula (V) which is key intermediate for the preparation of Diltiazem of formula (VI).

Yet another object of the present invention is to provide a process for the preparation of (αS, β-S)-β-[(2-aminophenyl)thiol]-α-hydroxy-β-(4-methoxyphenyl) propanoic acid alky ester of formula (V) from the cyclic sulfite or cyclic carbonate of formula (IV). The compound of formula (V) is a key intermediate in the production of Diltiazem of formula (VI).

DETAILED DESCRIPTION OF THE PRESENT INVENTION

The process of the present invention involves conversion of an optically pure 2R, 3S, or 2S, 3R-diol of formula (III), wherein $R^1$ is hydrogen or an alkyl, aryl, hydroxy, aryloxy, alkylthio, halo, or alkylamino residue, into a cyclic sulfite, or cyclic carbonate of formula (IV) by using an agent capable of introducing a sulfoxide or carbonyl group.

Accordingly, the present invention provides the novel compound of formula (IV).

The present invention also provides a process for the preparation of 5S-(p-alkoxphenyl)-4R-carboalkoxy-1,3,2-dioxathiolane-2-oxide, or the corresponding cyclic carbonate of formula (IV), and their optical recemate which comprises (a) treating an optically pure 2R, 3S or 2S, 3R diol of formula (III) with an agent capable of introducing a sulfoxide, or carbonyl group, in the presence of a base and an organic solvent, at a temperature in the range of −78° to 100° C.;

(b) resting the resultant mixture for a period of 1 to 15 hours;

(c) pouring the rested mixture into water; and (d) extracting the aqueous mure with an organic solvent to obtain the compound of formula (IV).

The agent which is capable of introducing the sulfoxide group can suitably be thionyl chloride, and the agent capable of introducing a carbonyl group can suitably be phosgene, diethyl carbonate, diphosgene, or triphosgene. Pyridine, triethylamine, or dimethylamino pyridine can be suitably employed as the base. The organic solvent used can suitably be selected from methylene chloride, chloroform, $CCl_4$, ethyl, acetate, ether, benzene, toluene, THF, and $CH_3CN$. The temperature of the reaction mixture can be suitably maintained between 0° to 20° C. The reaction mixture is suitably stirred for 1 to 12 hours.

The invention further provides a process for the synthesis of 2R-hydroxy-3S [(2-aminophenylthio)]-3-(p-alkoxyaryl) propanoic acid alkyl ester of formula (V) wherein $R_1$, $R^2$, $R^3$ are independently of each other methyl, ethyl, phenyl, naphthyl, methoxy, ethoxy, methylthio, ethylthio, chloro, fluro, bromo residue, and R is a methyl, ethyl, or benzyl residue.

The ester of formula (V) can suitably be prepared from the compound 5S(p-alkoxyaryl)-4R-carboalkoxy-1,3,2-dioxathiolane-2-oxide or its corresponding cyclic carbonate of formula (IV). Various substituted optically active cyclic sulfite esters or cyclic carbonate esters of formula (IV) where $R^1$ is a methyl, ethyl, propyl, naphthyl, phenyl, 1-2 naphthyl, methoxy, ethoxy, or phenoxy residue, and R is a methyl, ethyl, benzyl residue, were prepared by the method described hereinbelow, and the cyclic sulfites or cyclic carbonates were stereo- and regioselectively opened by a number of substituted 2-aminothiophenols or 2-aminothionaphthol reagents by refluxing in a suitable organic solvent to furnish a 2-aminoarylthio-α-hydroxy-β-(arylalkoxy)propionic acid alkyl ester of formula (V). The organic solvent can suitably be benzene, or toluene. The temperature is suitably maintained between 80° and 250° C. for 1–12 hours.

Accordingly the present invention, further provides a process for the synthesis of a 2R-hydroxy-3S-[(2-aminophenylthio)]-3-(p-alkoxyaryl)propanoic acid alkyl ester of formula (V) which comprises refluxing 2-aminothiophenol or 2-aminothionaphthol with 5S-(p-alkoxaryl)-4R-carboalkoxy-1,3,2-dioxa(thiolane)-2-oxide or the corresponding cyclic carbonate of formula (IV) in the presence of a solvent and an inert atmosphere and purifying the resultant compound of formula (V).

Refluxing can be carried out for a period of 1–26hours. Suitably benzene, toluene, xylene, p-dichlorobenzene, $CCl_4$, $CHCl_3$, DMSO, DMF, $H_2O$, acetone, ethanol can be used as solvent. The inert atmosphere is maintained by such as $N_2$, Argon or Helium. Purification can be carried out by e.g. crystalisation, or chromatography.

The temperature is suitably maintained between 80° and 250° C., and the refluxing is continued suitably for 1–12 hours.

The synthesis of an alkyl-(2R, 3S)-dihydroxy-3-(p-alkoxyaryl) propionate of formula (II) can be made by asymmetric dihydroxylation of a p-alkoxycinnamyl ester of formula (II)

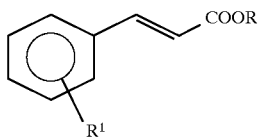

wherein $R^1$ is suitably an alkyl, alkoxy, aryloxy, or hydroxy residue, and E is an aryl, or alkyl residue, such as by the process described by Watson, K. G.; Fung, Y. M.; Gredley, M.; Bird, G. J.; Jackson, W. R.; Gountzos, H.; and Mattews, B. R. J., in Chem. Soc. Chem. Commun. 1990; 1018 by Fleming, P. R.; and Sharpless, K. B. J. in Org. Chem. 1991, Vol. 56, P. 2869; by Rama Rao, A. Ü.; Gaitonde, and A.; Rao, S. P., in Ind. Chem. 1992, Vol. 31B, P. 641.

The present invention also provides a process for preparing a compound of formula (VI) wherein $R^1$ is an alkyl, alkoxy, aryl, or aryloxy residue; $R^2$ and $R^3$ are independently of one another an alkyl, alkylamino, aryl alkylihio, or aryloxy residue by converting the compound of formula (V) into a compound of formula (VI).

A substituted benzaldehyde of formula (I)

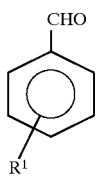

where $R^1$ is hydrogen or an alkoxy, alkyl or aryloxy residue, was treated with a substituted malonate reactant where R is an alkyl or aryl residue to yield the trans-p-alkoxy cinnamic ester of formula (II). The compound of formula (II) was subjected to asymmetric dihydroxylation to yield an alkyl-(2R,3S)-dihydroxy-3-(palkoxyaryl) propionate of formula (III). The diol of formula (III) was converted to a 5(S)-p-alkoxyphenyl)-4(R)-carboalkoxy-1,3,2-dioxathiolane-2-oxide of formula (IV) by treating with $SOCl_2$. That compound of formula (IV) was then treated with a substituted 2-amino thiophenol where $R^2$ and $R^3$ are independently of one another an alkyl, alkoxy, alkylamino, alkylthio, or aryl residue. The treatment is carried out at a temperature between 80° and 250° C., for 1 to 12 hours resulting in the production of a 2(R)-hydroxy-3(S)[(2-aminophenylthio)]-3-(p-alkoxyaryl) propionic acid alkylester of formula (V). The compound of formula (V) was converted to Diltiazem.

The present invention is further illustrated by the following examples.

EXAMPLE 1

Preparation of 5S-(p-methoxphenyl)-4R-carboethoxy-1,3,2-dioxathiolane-2-oxide of formula (IV) where R is ethyl $R^1$ is methoxy, and X is S)

To 2.4 g of a 1M solution in $CH_2Cl_2$ of 2R, 3S diol of formula (III) where R is ethyl, R' is methoxy. 2.4 ml pyridine was added, and the reaction mass was cooled to about 0° C., followed by slow addition of 0.8 ml thionyl chloride. After 12 hrs. the reaction mixture is poured into cold water and extracted with 3×25 ml of an organic solvent to furnish nearly quantative yield of the title compound. $[\alpha]^{22}D=113.3$ specific optical rotation was determined with 9 grams of the material dissolved in ethyl alcohol.

EXAMPLE 2

Preparation of 5R-(p-methoxyphenyl)-4S-carboethoxy-1,3,2-dioxathiolane-2-oxide of formula (IV), where R is ethyl, $R^1$ is methoxy, and X is S To 2.4 g of a 1M solution in $CHCl_3$ of a 2S, 3R diol of the compound of formula (III), wherein R is ethyl and R' is methoxy, 2.4 ml triethylamine is added and the reaction mass is cooled to about 20° C., followed by slow addition of 0.8 ml thionyl chloride. After 12 hours the reaction mixture is poured in cold water and extracted with 3×2.5 ml of an organic solvent to furnish the title compound of formula (IV) in an 88% yield.

EXAMPLE 3

Preparation of 5S-(p-methoxyphenyl)-4R-carbomethoxy-1,3,2-dioxathiolane-2-oxide of formula (IV) where $R^1$ is ethoxy, R is methyl, and X is S.

1.22 g dimethylaminopyridine is added to 2.26 g of a 1M solution in $CCl_4$ of a 2R, 3S diol of formula (III) where R is methyl, and R' is methoxy, and the solution is cooled to room temperature, followed by slow addition of 0.8 ml thionyl chloride. After 12 hours the reaction mixture is poured into cold water and extracted with 3×25 ml of an organic solvent, to produce of the title compound of formula (IV) in a yield of 90%.

EXAMPLE 4

Preparation of 5S-phenol-4R-carboethoxy-1,3,2-dioxathiolane-2-oxide of formula (IV), where $R^1$ is ethyl, R is H, and X is S 2.4 ml pyridine was added to 2.1 g of a 1M solution in ethyl acetate of a 2R, 3S diol of formula (III) wherein R is ethyl $R^1$ is H. The solution was cooled to about 20° C., followed by slow addition of 0.8 ml thionyl chloride. After 3 hours resting the reaction mixture is poured in cold water and extracted with 3×25 ml organic solvent. The title compound was obtained with 92% yield.

EXAMPLE 5

Preparation of 5S-(p-methoxypheny)-4R-carboethoxy-2-oxo-1,3-dioxolane of formula (IV) where $R^1$ is methoxy, R is ethyl, and X is C 2.4 ml triethylamine was added to 2.4 g of a 1M solution in toluene of a 2R, 3S-diol of formula (III) where R is ethyl and $R^1$ is methoxy, and the solution was cooled to about 0° C., followed by slow addition of 1 ml 1M solution of phosgene in toluene. After 8 hours, the reaction mixture was washed with cold water and the aqueous phase was extracted with 3×25 ml organic solvent to furnish the title cyclic carbonate of formula (IV) in a 90% yield.

EXAMPLE 6

Preparation of 2R-hydroxy-3S-[(2-aminophenylthio)]-3-(p-methoxphenyl) propanoic acid ethyl ester of formula (V), where $R^1$ is methoxy, $R^2$ and $R^3$ are H, and R is ethyl 1.07 ml of 2-aminothiophenol was added to 2.86 g of a solution in 20 ml toluene, of a 4R, 5S dioxathiolane of formula (IV) where X is S, R is ethyl, and R' is methoxy, and the solution was refluxed for 4 hours under an argon atmosphere, and then the solvent was removed. After chromatography the residue yielded 80% of the title compound, having a melting point of 115° C., $[\alpha]D^{22}=+266.1$ (c, 1.23, EtOH).

EXAMPLE 7

Preparation of 2R-hydroxy-3S-[(2-aminophenylthio)]-3-(p-methoxyphenyl) propanoic acid methyl ester of formula (V), where $R^1$ is methoxy, $R^2$ and $R^3$ are H, and R is methyl.

1.07 ml 2-aminothiophenol was added to a 20 ml solution is xylene of 2.72 g of an 4R, 5S dioxathiolane of formula (IV) where X is S, R is methyl and R' is methoxy. The solution was refluxed for 4 hours under a $N_2$ atmosphere, and then the solvent was removed. After chromatography the residue provided the title compound in a 82% yield.

EXAMPLE 8

Preparation of 2R-hydroxy-3S-[(2-aminonaphthylthio)]-3-(p-methoxyphenyl) propanoic acid ethyl ester of formula (V) where R is methoxy, $R^2$ and $R^3$ are 1,2-naphthyl, and R is ethyl.

1.75 g 2-aminothionaphthol was added to a solution in 20 ml o-dichlorobenzene of 2.86 g a 4R, 5S dioxathiolane of formula (IV) where R is ethyl, X is S, and R' is methoxy, and the reaction mass was heated at about 120° C. for 4 hours. The solvent was removed under an argon atmosphere. After chromatography of the residue of the title compound was obtained in a 78% yield.

EXAMPLE 9

Preparation of 2R-hydroxy-3S-[(2-aminophenylthio) ]-3-(p-methoyphenyl) propanoic acid ethyl ester of formula (V), where $R^1$ is methoxy, $R^2$ and $R^3$ are H, and R is ethyl.

1.07 ml of 2-asminothiophenol was added to 20 ml of a solution in toluene of 2.66 g of a 4R, 5S 2-oxo-dioxolane of formula (IV) where X is C, R is ethyl, and $R^1$ is methoxy, and the solution was then refluxed for 4 hours under an argon atmosphere, then the solvent was removed. After chromatography of the residue of the title compound was obtained in a 80% yield, having a melting point of 115° C., $[\alpha]D^{22}$=+266.1 (c, 1.23, EtOH).

We claim:

1. A compound of formula (IV)

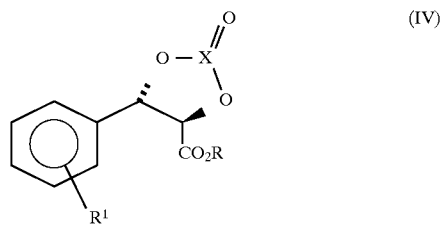

which is 5S-p-methoxyphenyl-4R-carboethoxy 1,3,2-dioxathiolane-2-oxide, or a 5S-p-methoxyphenyl-4R-carboethoxy-2-oxo-1,3-dioxolane in which $R^1$ is methoxy, R is ethyl, and X is S or C.

2. A process for preparing a compound of claim 1, which comprises:

(a) treating an optically pure 2R, 3S or 2S, 3R diol of formula (III)

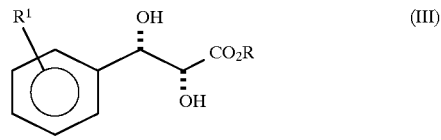

wherein R is ethyl, and $R^1$ is methoxy, with an agent capable of introducing a sulfoxide or carbonyl group in the presence of a base and organic solvent at a temperature in the range of −78° to 100° C.;

(b) resting the resultant reaction mixture for a period of 1 to 15 hours;

(c) pouring the rested mixture in water; and (d) extracting with organic solvent to yield a dioxathiolane of formula (IV).

3. The process of claim 1 wherein the agent capable of introducing sulfoxide is $SOCl_2$, or sulfuryl chloride.

4. The process of claim 1 wherein the agent capable of introducing carbonyl group is phosgene, triphosgene, diethyl carbonate, or diphosgene.

5. The process of claim 1 wherein the agent capable of introducing sulfoxide is thionyl chloride, and wherein the agent capable of introducing carbonyl group is phosgene, and said agent is added to the compound of formula (III) at once or dropwise over a period of between 15 minutes to 6 hours.

6. The process of claim 5, wherein the product obtained after the addition of thionyl chloride, or phosgene is rested for a period of 1 to 15 hours.

7. The process of claim 2 wherein said organic solvent is $CH_2Cl_2$, $CHCl_3$, ethyl acetate, $CCl_4$, $CH_3CH$, toluene, or THF.

* * * * *